United States Patent [19]

Swanson

[11] Patent Number: 4,546,642

[45] Date of Patent: Oct. 15, 1985

[54] ACCELERATED HEART VALVE TESTING APPARATUS AND METHODS

[75] Inventor: Wilbur M. Swanson, St. Louis County, Mo.

[73] Assignee: Dynatek, Inc., St. Louis, Mo.

[21] Appl. No.: 641,870

[22] Filed: Aug. 17, 1984

[51] Int. Cl.$^4$ ................................................ G01N 3/36
[52] U.S. Cl. ........................................ 73/37; 73/168; 73/812
[58] Field of Search ................... 73/3, 168, 48, 46, 812

[56] References Cited

U.S. PATENT DOCUMENTS

| 4,381,663 | 5/1983 | Swanson | 73/37 |
| 4,450,710 | 5/1984 | Nettekoven | 73/37 |

Primary Examiner—Stewart J. Levy
Assistant Examiner—Hezron E. Williams
Attorney, Agent, or Firm—Kalish & Gilster

[57] ABSTRACT

Apparatus and methods for durability (fatigue) testing of prosthetic heart valves or other check valves. The apparatus is circular in plan and includes a test fixture in which the valves are circularly arranged, located with communicating passages, such passages communicating with bellows closed at one end. The bellows are carried by a swash plate journalled to a motor by a coupling providing an adjustable tilt axis. The tilt axis determines the amplitude of the motion or flow of the fluid, as the bellows alternately expand and contract. A central bypass chamber includes orifices which are selectively varied in effective cross section to control an amount of the test fluid which bypasses the test samples, thereby determining fluid pressure differential across the sample valves. Fluid in the apparatus can be heated by an electric heater to temperatures similar to human blood, a temperature probe monitoring the temperature for its control. A pressure tap monitors the fluid pressure for shutting down the apparatus if abnormal pressures or leaks are developed. Several prosthetic heart valves, e.g., two, four, six, eight, etc., are held by the fixture at the same time for life testing at relatively high cyclic rates.

14 Claims, 5 Drawing Figures

1

ACCELERATED HEART VALVE TESTING APPARATUS AND METHODS

BACKGROUND AND SUMMARY OF THE INVENTION

The present invention relates to the testing of prosthetic heart valves, or similar valves.

Representative of the prior art is Swanson U.S. Pat. No. 4,381,663, in which are set forth apparatus and methods by which test samples such as heart valves are tested in a closed fluid environment by oscillating flow of a bellows-actuated fluid oscillator.

A particular need arises in the durability-fatigue testing of biological tissue prosthetic heart valves. To be tested properly such heart valves may be conducted in a sterile human blood plasma environment at normal body termperature, 37° C.

In the testing of such heart valves, it may be desired to carry out a testing of several at the same time. The valves may vary from valve to valve, and it is desirable to be able to test each under the same operating conditions so as to achieve a desired degree of control for comparative purposes.

Accordingly, it is an object of the present invention to provide an improved apparatus for testing of heart valves by the provision of a system making closed durability, or fatigue tests on a number of different samples at the same time.

Specifically, an object of the present invention is the provision of such apparatus and methods for testing of prosthetic heart valves in a sterile blood plasma, or other fluid environment at body temperature.

It is another object of the invention to provide such testing apparatus and methods for carrying out the testing of heart valves in a preselected fluid medium at a desired temperature.

It is also an object of the present invention to provide such apparatus wherein testing may be carried out automatically and without supervision with assurance that testing of the apparatus will automatically terminate in the event of a failure, undesired condition, excessive temperature or the like.

Yet another object of the invention is the provision of such testing apparatus and methods which provide repetitive stressing of the heart valve at a high frequency which may be considerably greater than that at which the sample under test would normally be flexed in use, thereby greatly accelerating the life testing of such sample.

Another object of the invention is the provision of such testing apparatus and methods wherein a number of different valves being tested at one time may be varied from test to test, and wherein the number of samples under test does not influence the test conditions in a deleterious or disadvantageous way.

The invention has as another object the provision of such testing apparatus and methods which are extremely compact and which minimize the volume of test fluid being utilized, as well as minimizing the cubage of the apparatus, and providing apparatus which operates with extreme efficiency and little input power.

Yet another object of the invention is the provision of such test apparatus and methods which allow substantial variation in the amplitude of the stresses applied to the sample during test, and permitting the amplitude to be very readily and easily changed without disturbance of other aspects ot the test, while providing nevertheless testing apparatus and methods which permit a wide range of testing conditions, including different termperatures, pressures, frequencies and stresses.

Among still other objects of the invention include the provision of such testing apparatus which: provides testing in a completely sealed fluid environment; economizes in the use of test fluids; provides extremely high test visablility and ease of insertion and removal of test samples and high accessibility thereof; permits test fluid to be easily filled, emptied and/or removed, and facilitates cleaning of the apparatus.

Briefly, valve testing apparatus for testing of test samples, i.e., valves, in accordance of the invention by application of repeated oscillatory forces produced by fluid motion relative to the sample includes a chamber for receiving a plurality of test samples, the chamber being such as to define individual fluid flow passages communicating with respective test samples for directing an oscillating flow of fluid of such test samples. Plural bellows are connected with each of the respective fluid flow passages, with which they are arranged in a circular pattern, and a swash plate is positioned below the bellows, with means for rotatably driving the swash plate oscillatorily to provide corresponding alternate expansion and contraction of the bellows. A further fluid passage is connected with the test samples for providing a fluid path extending from one of the bellows, into the test sample, through the further fluid passage, through another test sample, and to another bellows, by the opposite side of the swash plate. The swash plate, with adjustable tilt axis, causes alternate contraction and expansion of the bellows on opposite sides of the swash plate to alternately expose the test samples to oscillatory fluid forces.

A bypass passage carries the flow while a valve is closed. The inertial reaction of the fluid in this passage during flow acceleration determines the pressure loading on the valve.

An electric heating device and a temperature probe are utilized for controlling the temperature of the fluid in the apparatus, such as to provide, for example, tests under conditions typical of the human blood plasma environment at 37° C.

Other objects and features will be in part apparent and in part pointed out hereinbelow.

BRIEF DESCRIPTION OF THE DRAWINGS

Corresponding reference characters indicate corresponding parts throughout the views of the drawings.

DESCRIPTION OF THE PREFERRED EMBODIMENT

Figure 1:
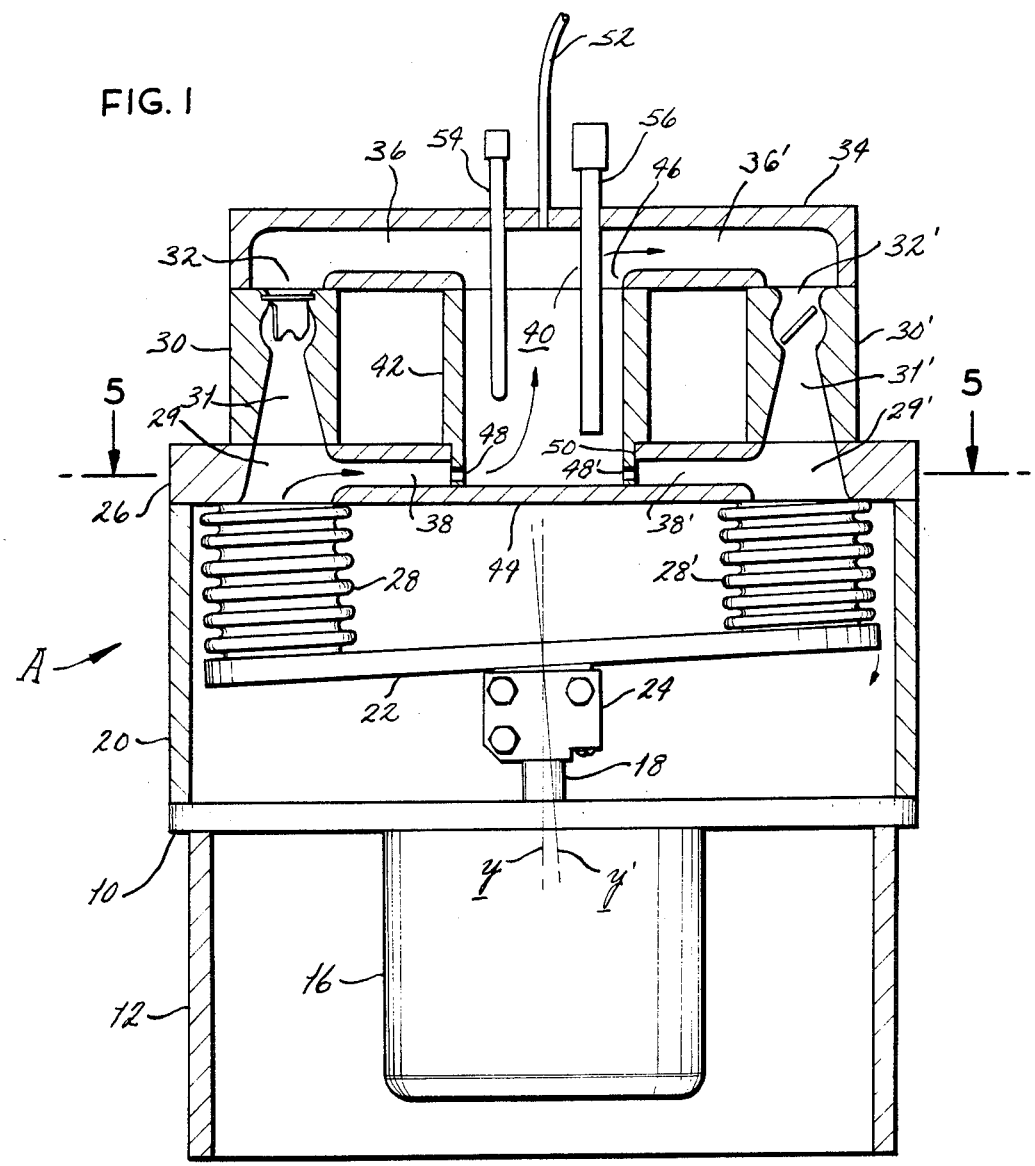
FIG. 1 is a vertical cross-section of testing apparatus constructed in accordance with and embodying and carrying out the present invention.

Referring now to the drawings, there is illustrated generally at A a system according to an embodiment of the invention for carrying out durability or fatigue tests of fluid valves and especially prosthetic heart valves.

System A constitutes a bellows-actuated fluid oscillator for cycling fluid at a frequency of from several hundred to several thousand cycles per minute in a completely closed liquid condition for repeatedly exposing the sample under test to the action of an oscillatory fluid on opposite sides of the sample. The action involves all three of: (1) forces; (2) inertia; and (3) flow.

System A is a closed system, as noted, wherein the fluid utilized as a test medium is not exposed to atmosphere or other oxidizing or non-sterile factors. If the test samples constitute prosthetic heart valves, the test fluid may be sterile human blood plasma heated to a body-simulative temperature, e.g., the normal body temperature 37° C., or other suitable fluids.

Referring primarily to FIG. 1, a base plate 10 of circular shape in plan is suitably supported by a cylindrical base 12. Carried centrally by and extending below base plate 10 is a drive motor 16 such as of, for example, controllable speed DC type to provide rotation of its output shaft 18 at a preselected angular velocity. A cylindrical housing 20 extends above base plate 20 for enclosing a swash plate 22 adapted for being rotated by shaft 18 by means of a rotatable tilt coupling 24, the features of which are described in greater detail below.

A so-called port plate 26 of circular periphery extends across the top of housing 20 and, as will be hereinbelow apparent, is radially ported for fluid communication between bellows 28, 28' carried by swash plate 22 and valve chambers as at 30, 30' in which are provided test samples, as at 32, 32' such as prosthetic heart valves which are to be tested by the repeated oscillatory forces produced by fluid motion relative to such testing samples simulative of the action of blood as it is pumped in the human heart, as produced in passages 29, 29'.

Extending across the top of test or valve chambers 30, 30' is a top plate 34 of circular shape and plan, through which is provided a passage 36 for flow of fluid from one test sample, such as 32, across to the other test sample, 32'. Thus, it will be understood that a fluid path is completed between the opposite bellows 28, 28' including fluid passages 31, 31' in the test fixtures or valve chambers 30, 30' and also through passage 36. However, in accordance with the invention, each of said passages 31, 31' has connected with it a respective radial bypass port 38, 38' for providing connection to a central bypass passage 40. Passage 40 is formed by a cylindrical sleeve 42 closed at its bottom end by a bottom wall 44 of port plate 26 and opening at its upper end into a central aperture 46 for communication with passage 36.

Although but two bellows 28, 28' and two valve or sample chambers 30, 30' are shown in FIG. 1, it will be understood that the invention contemplates the provision of a plurality of such chambers and bellows, such as two, four, six or eight in number, evenly and circularly spaced about the axis defined by motor shaft 18.

Sleeve 42 constitutes a central bypass chamber to which fluid is selectively admitted from the respective bellows upon rotation of swash plate 22, compressing each bellows in turn. As each bellows is compressed, fluid is bypassed through throttle valve orifices 48, 48' which are located in a reduced thickness portion 50 of sleeve 42 and which are adapted to restrict the flow of bypass according to the positioning of sleeve 42 relative to passages 38, 38', as explained below. Communicating essentially with bypass passage 36 and also with the bypass chamber 40 is a pressure line or tap 52 for connection with a conventional pressure switch (not shown) such as operative for turning off motor 16 and otherwise disabling apparatus A if the pressure should exceed a predetermined maximum safe value, or decrease below a minimal set value if a leak occurs. Extending into chamber 40 is a temperature sensor 54 for monitoring the temperature within chamber 40 and, thus also, the temperature of the fluid circulating within the system. Also extending into chamber 40 is an electric heater 56 which by conventional control interconnection with temperature probe 54 may be switched on or off cyclically as necessary to maintain the fluid within the apparatus substantially as a predetermined temperature such as normal body temperature at 37° C. The appropriate pressure-responsive switch (not shown) interconnected with pressure tap 52 may be also operative to turn off the source of electric power for heater 56 if the internal pressure should change abnormally, thereby preventing leakage of fluid from the apparatus.

Figure 5:
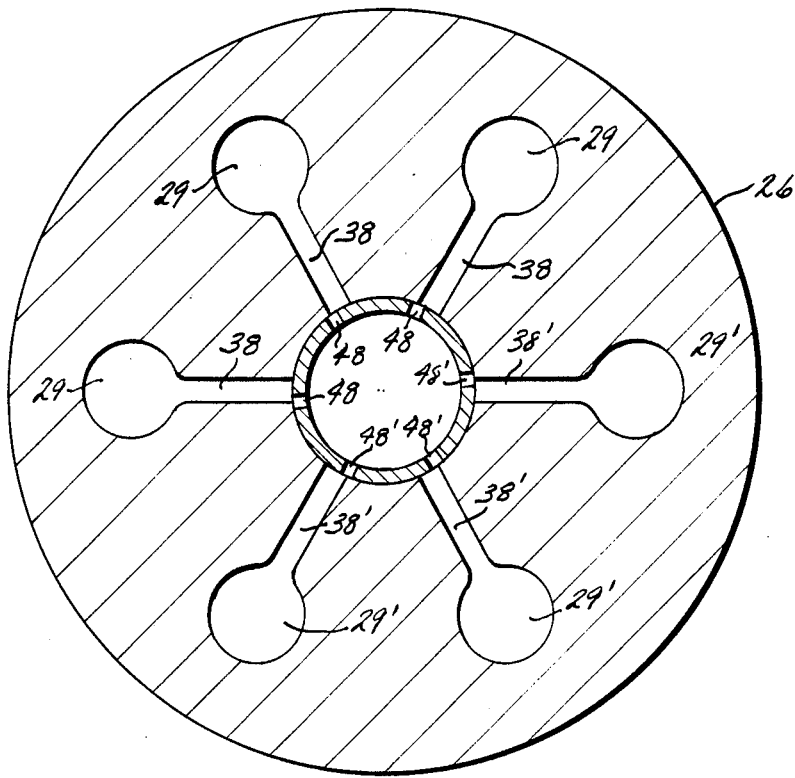
FIG. 5 is a horizontal cross-section of the apparatus of FIG. 1, as taken generally along line 5—5.

Referring to FIG. 5, sleeve 42 is centrally located within the port plate 26 and equidistant from each of the passages 29 which receive fluid relative to the bellows 28, 28'. Passages 38, 38' extend radially toward sleeve 42 and communicate with bypass chamber 40 of said sleeve through throttle valve control orifices 48, 48', which are shown slightly offset relative to the passages 38, 38', whereby such orifices are partly blocked by the port plate relative to such passages. Sleeve 42 may be rotationally shifted, when apparatus is partly disassembled on its elements loosened relatively, to move the orifices 48, 48' more or less into alignment with the passages 38, 38'. This movement controls the effective size of the orifices and consequently provides greater or lesser closing pressure difference across the valves.

It will be understood that, during operation, pressure developed by the bellows will be such as to cause a net positive flow from the respective bypass passages 38, 38' into the bypass chamber 40 and thereby such fluid will bypass the test valves 32, 32'. A bypass pressure differential can thereby be precisely controlled to predetermine the closing valve pressure developed at each test valve during cycles of operation.

Figure 2:
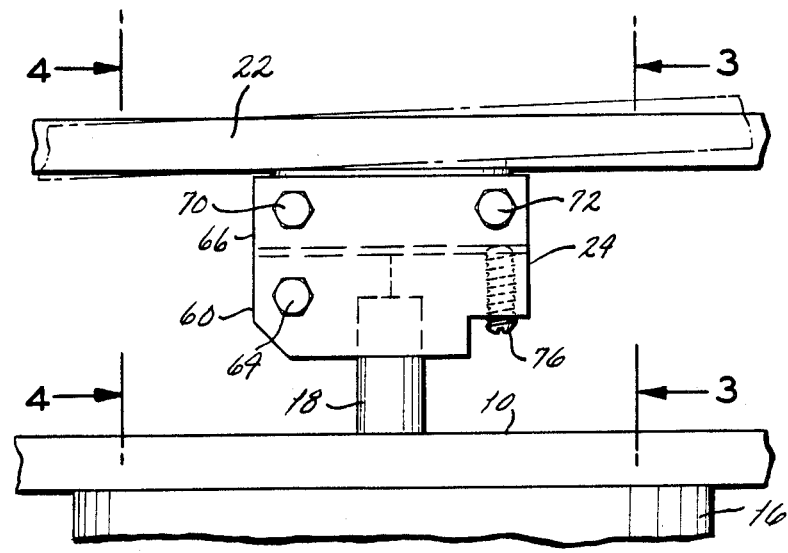
FIG. 2 is an enlarged side view of portions of a certain swash plate rotating mechanism of the apparatus of FIG. 1.
Figure 3:
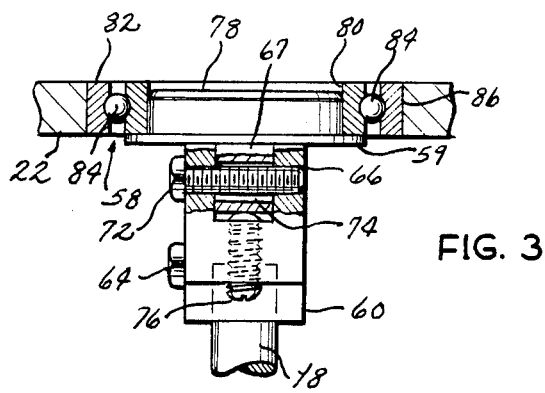
FIG. 3 is a vertical cross-section taken generally along line 3—3 of FIG. 2.
Figure 4:
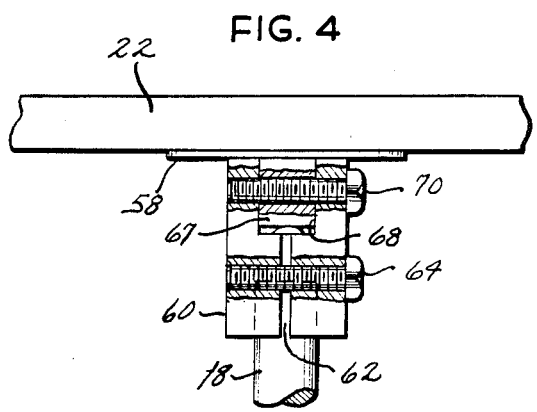
FIG. 4 is a similar vertical cross-section, but from an opposite view, and as taken generally along line 4—4 of FIG. 2.

Tilt coupling 24 is show in greater detail in FIGS. 2-4. Generally, coupling 24 is rotatably journalled to swash plate 22 to produce the rotational tilting of swash plate 22 without actual rotation, yet with a controlled degree of tilt, providing a tilt axis Y' relative to normal Y.

The extent of contraction and expansion with each of the bellows 28, 28' alternately undergoes is thereby predetermined, the coupling 24 being adjustable for this purpose, as explained shortly. FIG. 3 illustrates that swash plate 22 is provided with a ball bearing assembly 58 by which the coupling 24 is journalled to swash plate 22, producing such tilting.

More specifically, and referring also to FIG. 4, coupling 24 has a lower half or so-called U-base member 60 which is bored to accept motor shaft 18. Member 60 is vertically slotted at one side only, as shown at 62, with such slot extending through to the bore for the motor shaft. Clamping bolt 64 is threaded laterally through the slotted portion of member 60 for clamping it tightly to motor shaft 18. An upper portion 66 of the coupling is provided with a tongue 67 fitted within a U-shaped recess 68 of portion 60 and is maintained in pivotal relation within recess. Another bolt 72 is threaded through the upper portion 66 at the other end of the aperture through tongue 67, but the tongue 67 is slotted, its slot 74 opening downwardly, to permit tongue 67 to pivot upwardly about pivot bolt 70 and to be tilted by an amount determined by a jack screw 76. After the desired extent of tilt has been achieved by adjustment of jack screw 76, bolts 64, 70, and 72 all are tightened.

Tongue 67 supports a bearing hub 78 having a bearing retainer flange 59, the hub being fitted within the inner race 80 of bearing 58. Outer race 82 rotates relative to the inner race 80 over ball bearings 84, which race 82 is set within a central recess 86 of swash plate 22. Accordingly, as tilt coupling 24 is rotated by the motor shaft 18, swash plate 22 is given a rotary-tilt motion without itself rotating. Such motion causes oscillation of the bellows 28, 28' to provide pumping action by which each of the test samples are, in sequence, each provided with fluid under pressure and then, on the alternate half of each cycle, are exposed to a negative pressure. Each test valve is thereby cycled during each rotation of motor shaft 18. Accordingly, the angular velocity of shaft 18 determines the cycle rate of each test valve. As the number of test valves may be as many as four, six, eight, etc., each such rotation of shaft 18 cycles a multiplicity of test samples, and with the displacement drive amplitude being determined by the degree of tilt provided by coupling 24 thereby to predetermine the flow rate through each test valve. As explained above, the pressure to which each test valve is exposed is determined by the positioning of the throttle valve orifices 48, 48'.

The novel packing geometry and arrangement of elements thereby provides simultaneous testing of a multitude of test valves, which may be any of various types, but the packing geometry for testing of prosthetic heart valves is such that six testing chambers 31, 31' provides an optimum number.

The extreme compactness of new apparatus A greatly minimizes the volume of the testing fluid utilized such as blood plasma or serum. Further, since the fluid is exposed to a limited surface area within the apparatus, there is very little friction as the test fluid oscillates therein, with consequent negligible frictional heating of the fluid. The low fluid and mechanical mass of apparatus A provides oscillation at a relatively high frequency of, for example, 1000-2000 cycles per minute and with very little driving power being required.

Furthermore, the system is completely sealed, there being no contact with the test fluid with the ambient environment. Accordingly, for the durability-fatigue testing of prosthetic heart valves, the new apparatus is extremely advantageous.

In operation, swash plate 22 first undergoes tilting movement from the position shown in FIG. 1, causing compression of bellows 28. The test fluid, such as blood plasma, is pumped up into the left valve chamber 31, thus closing valve 32, and exits through the bypass port 38 and its associated throttle valve control orifice 48. The inertial pressure drop through such port or orifice 48 is communicated to the closed valve 32' and produces closing pressure for the latter. The exit flow thus is through chamber 40 and down through valve 32' in accordance with the fluid motion shown by arrows in FIG. 1. Adjustment of sleeve 42 controls the effective cross section of each such orifice. Accordingly, the pairs of test samples alternately undergo closing and opening, inasmuch as the tilt and flow processes are reversed as the rotary-tilt movement of swash plate 22 results in tilting of the plate such as will compress bellows 28' and elongate bellows 28', each as once more shown in FIG. 1.

In addition to providing a highly useful apparatus, the invention may be noted as also being methodo-logically innovative. Thus, there is provided a new method of durability testing of check valves. Further, the novel use of a swash plate to cause alternate expansion and contraction of the bellows at opposite sides of the swash plate provides an arrangement which is at once suited both for testing only a pair of test samples as well as for multiple pairs of such samples, such as two, four, six, etc., as hereinabove explained, and thereby permitting a single motor to be utilized regardless of the number of test valves.

In view of the foregoing, it will be seen that the several objects of the invention and other advantages are achieved by the new constructions and methods which have been described.

Although the foregoing includes the description of the best mode of the embodiments contemplated for carrying out the invention, various modifications are contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. Valve testing apparatus for testing of check valves such as prosthetic heart valves by application of repeated oscillatory flows produced by fluid motion relative to the valves, said apparatus comprising chamber means for receiving a plurality of test samples comprising valves to be tested, said chamber means defining fluid flow passages communicating with the valves for directing an oscillating flow of fluid to said test samples, at least first and second bellows respectively connected with the fluid flow passages, and a swash plate carrying the bellows, means for rotatably driving the swash plate for producing rotatably tilting oscillatory movement of the bellows, and a further fluid passage connecting the test samples for providing a fluid path extending between the bellows and including bypass passage means for receiving fluid from each of the passages respectively communicating with the bellows, and bypass flow control means, for selectively permitting the fluid to bypass the respective test valves through the bypass passages means thereby to control the fluid pressure to which the valves undergoing testing are exposed.

2. Valve testing apparatus according to claim 1 and further characterized by the bypass control means providing for branching of fluid from the respective bellows upon contraction thereof whereby a portion of the fluid flows into and closes a valve undergoing testing and another portion bypasses such valve by flowing through a bypass path, the amount of flow in said bypass path determining the closing pressure for such valve, said bypass path permitting fluid flow also to the inlet of a second one of the valves for ultimate flow into the other of the bellows upon expansion thereof, the bypass path being defined in part by a central bypass chamber.

3. Valve testing apparatus according to claim 2 and further characterized by temperature control means for providing heat transfer with respect to the fluid in said central bypass chamber for maintaining the fluid at a predetermined temperature.

4. Valve testing apparatus according to claim 3 and further characterized by the temperature control means including at least one temperature probe extending into the central bypass chamber, the heat transfer means comprising an electric heater extending into the bypass chamber.

5. Valve testing apparatus according to claim 2 and further characterized by the bypass passage means including individual bypass ports communicating with the fluid flow passages, the central bypass chamber being of volume substantially larger than the fluid flow passages and communicating with each of the individual ports.

6. Valve testing apparatus according to claim 2 and further characterized by the central bypass passage being centrally located relative to the fluid flow passages, bypass flow control means for communicating with respective ones of the individual bypass ports for causing a predetermined inertial pressure differential across the flow control means comprising orifices selectively changeable for controlling restriction of bypass port fluid flow.

7. Valve testing apparatus according to claim 6 and further characterized by said bypass flow control means comprising a cylindrical body including such orifices and changeable by rotation relative to said individual bypass passages for selectively limiting the effective area the orifices.

8. Valve testing apparatus according to claim 1 and further characterized by said means for driving the swash plate comprising a motor and a rotating-tilt coupling interconnecting the motor with the swash plate, the coupling being of adjustable tilt nature for defining a tilt axis for the swash plate to produce a predetermined drive displacement amplitude produced by oscillatory tilting movement of the swash plate upon motor operation.

9. Valve testing apparatus according to claim 8 and further characterized by the rotating-tilt coupling being rotatably journalled to the swash plate, the motor including a shaft carrying the rotating-tilt coupling whereby oscillatory movement of the swash plate is produced upon rotation of the motor shaft, the rotating-tilt coupling producing a tilt axis for the swash plate forming a predetermined angle with the longitudinal axis of the motor shaft.

10. Valve testing apparatus according to claim 2 and further characterized by the chamber means for receiving test valves being spaced at intervals about a circle, the means for rotatably driving the swash plate being an electric motor having a shaft rotating about an axis extending through the center of the circle, the bypass chamber bing defined by a cylindrical body located centrally with respect to the swash plate and connected by individual bypass ports with the respective fluid flow passages.

11. A method of durability testing of check valves such as prosthetic heart valves including positioning of at least one pair of such test valves with opposite orientations proximate the opposite ends of a fluid path for bidirectional exposure to oscillating movement of fluid in the fluid path, including imparting rapid oscillating movement of said fluid in the path with respect to the test valves, and characterized by permitting the fluid to bypass the test valves according to a predetermined inertial pressure differential, thereby to control the pressure of the oscillating fluid forces to which the test valves are exposed upon oscillation of the fluid.

12. A testing method of according to claim 11 and further characterized by the imparting of rapid oscillating movement of the fluid being effected by causing alternate contracting and expanding of bellows at the opposite ends of the fluid path, including locating the bellows at opposite sides of a swash plate, and causing the swash plate to undergo a rotary-tilt oscillatory motion but without causing rotation of the swash plate.

13. A testing method according to claim 12 and further characterized by controlling the amplitude of oscillation of the rotary-tilt motion by changing tilt axis of the swash plate, thereby to control the amplitude of oscillatory movement of the fluid.

14. A testing method according to claim 13 wherein the fluid comprises blood plasma or other suitable fluids and the test samples are prosthetic heart valves.

* * * * *

UNITED STATES PATENT AND TRADEMARK OFFICE
CERTIFICATE OF CORRECTION

PATENT NO. : 4,546,642

DATED : October 15, 1985

INVENTOR(S) : Wilbur M. Swanson

It is certified that error appears in the above-identified patent and that said Letters Patent is hereby corrected as shown below:

Column 8, Claim 14, line 42, "samples" should be ---valves---.

Signed and Sealed this

Thirty-first Day of December 1985

[SEAL]

Attest:

Attesting Officer

DONALD J. QUIGG

Commissioner of Patents and Trademarks